United States Patent [19]

Steinbichler et al.

[11] Patent Number: 4,964,770
[45] Date of Patent: Oct. 23, 1990

[54] PROCESS OF MAKING ARTIFICIAL TEETH

[76] Inventors: Hans Steinbichler, Am Bauhof 4 8201, Neubeuern; Jürgen Willer, Payerstrasse 30 7410, Reutlingen, both of Fed. Rep. of Germany

[21] Appl. No.: 218,101
[22] Filed: Jul. 12, 1988

[30] Foreign Application Priority Data

Jul. 16, 1987 [DE] Fed. Rep. of Germany ....... 3723555

[51] Int. Cl.$^5$ ............................................. A61C 5/10
[52] U.S. Cl. ................................. 433/223; 433/214; 356/376
[58] Field of Search ............... 433/218, 219, 223, 214, 433/215, 213, 229; 356/376

[56] References Cited

U.S. PATENT DOCUMENTS

| | | |
|---|---|---|
| 3,861,044 | 1/1975 | Swinson, Jr. . |
| 4,182,312 | 1/1980 | Mushabac . |
| 4,575,805 | 3/1986 | Moermann et al. ................ 433/223 |
| 4,611,288 | 9/1986 | Duret et al. ......................... 364/474 |
| 4,663,720 | 5/1987 | Duret et al. ......................... 433/214 |
| 4,821,200 | 4/1989 | Öberg ................................. 356/376 |
| 4,837,732 | 6/1989 | Brandestini et al. ................ 433/223 |

FOREIGN PATENT DOCUMENTS

| | | |
|---|---|---|
| 0054785 | 6/1982 | European Pat. Off. . |
| 0091876 | 10/1983 | European Pat. Off. . |
| 0110797 | 6/1984 | European Pat. Off. . |
| 0040165 | 10/1985 | European Pat. Off. . |

OTHER PUBLICATIONS

J. P. Duncan et al, "Moiré Contourgraphy and Computer-Aided Replication of Human Anatomy", IMechE, vol. 9, No. 1, pp. 29–36, Jan. 1980.

Primary Examiner—Cary E. Stone
Attorney, Agent, or Firm—Dilworth & Barrese

[57] ABSTRACT

In a process of making artificial teeth horizontal or other contour lines are generated on the ground tooth stump and on adjacent surfaces, said lines are detected by optoelectronic means, the data which have thus been acquired are used to compute the three-dimensional shapes of the tooth stump and of the required artificial tooth, and an artificial tooth having the shape which has thus been determined is then made by processes known per se.

12 Claims, 1 Drawing Sheet

PROCESS OF MAKING ARTIFICIAL TEETH

BACKGROUND OF THE INVENTION

1. Field of the Invention

This invention relates to a process of making artificial teeth.

2. Description of the Prior Art

In the previously conventional process of making artificial teeth, the clinical conditions in the mouth of the patient are reproduced in that impressions are taken and are used to make patterns. A process of making artificial teeth must ensure that the artificial teeth which are made will exactly fit because such exact fit is required for a safe anchoring and a permanent retention of the artificial teeth or the dentures comprising such teeth so that all tissues which are involved in the chewing operation will be able to take up the physiological loads without suffering damage.

All operations performed by the dentist and all operations which are subsequently performed by the dental technician in the making of artificial teeth are performed by methods which have been used for decades and will now briefly be described with reference to the provision of an individual crown:

(1) An impression from the tooth stump which has been prepared is taken by means of a rubber-elastic or hydrocolloidal impression-taking material;

(2) The tooth stump is temporarily protected;

(3) A superhard gypsum is cast into the impression and a working pattern as well as a counterbite pattern are made;

(4) The patterns are installed in an articulator;

(5) An artificial crown is cast from metal in a mold prepared by means of a wax pattern, (6) The casting is fitted on the tooth stump in the mouth and the artificial crown is finally fixed.

That conventional making of artificial teeth from metal or other materials requires a large number of operations to be performed by the dentist and the dental technician. Said operations involve a risk of a large number of inaccuracies and errors so that an exact fit of the artificial tooth or teeth may not be obtained and the operations may have to be repeated.

These disadvantages may be due to properties of the materials employed, such as the tendency of gypsum to expand and the tendency of metal to shrink, but may also be due to improper work and to difficult conditions in the mouth.

For some time it has been endeavored to replace the conventional taking of an impression and the succeeding operations by other techniques, which depend on the use of mechanical or optical three-dimensional measuring and scanning means. The informations which have thus been obtained are stored and are delivered to control devices of numerically controlled machine tools which have already been introduced for general machining operations.

U.S. Pat. No. 4,182,312 illustrates a mechanical scanning to obtain information on three-dimensional surfaces of teeth and surrounding tissue directly from the patient. For that purpose a probe is moved by the dentist in the patient's mouth. But inaccuracies will always be involved in mechanical scanning.

In the process described in U.S. Pat. No. 3,861,044 a cavity of a tooth is photographically recorded and the dentist shapes a filling body of wax to give it the desired final shape.

In the method described in European Patent 0.054 785, corrections of shape are also required before the fit is as exact as is required. Before such shaping, the three-dimensional and topographic shape of surfaces of organs of the body is optically detected without contacting them.

In the process disclosed in European Patent 0 040 165 it is endeavoured to obtain data of a prepared tooth stump by holographic interferometry and to transmit such data. Light that is generated by a laser is subjected to optoelectronic processing and the resulting data are delivered to a computer. Whereas that process has been described in European Patent 0 040 165, such process has not yet been performed in practice.

SUMMARY OF THE INVENTION

It is an object of the invention to provide for the making of artificial teeth a simple and fast process which can be performed in practice.

In accordance with the invention that object is accomplished in that horizontal or other contour lines are generated on the ground tooth stump and on adjacent surfaces, said lines are detected by optoelectronic means, the data which have thus been acquired are used to compute the three-dimensional shapes of the tooth stump and of the required artificial tooth, and an artificial tooth having the shape which has thus been determined is then made by processes known per se.

In the process in accordance with the invention, horizontal or other contour lines must be generated on the tooth stump. From the process described in European Patent 0 040 165 the invention basically differs in that an optical method is used to generate horizontal or other contour lines.

The shape of the ground teeth stump and the shape of the adjacent and antagonistic teeth are represented by horizontal or other contour lines, which by methods known per se are generated, e.g., by projection, or are detected with utilization of the moiré effect.

In the projection method, contour lines, i.e., lines representing the external shape of the tooth stub, are generated projection (FIG. 1). The contour lines may be generated by interferometric methods performed by means of a laser or by shadow projection. To utilize the moiré effect, the tooth stump is illuminated through a grating by means of a television camera which is spaced from the light source. The superposition of the shadow pattern projected on the tooth stump and of the image of the grating will result in the generation of a moiré pattern, which represents the contour of the tooth stub (FIG. 2).

The contour lines may be detected by means of a video camera either directly or by means of optical glass fibers.

The contour line data are processed in an image processing system. That processing differs from line-tracking programs in that the processing is based on an intensity measurement, which can easily be performed by a television camera. Intensity data for all picture elements are contained in the video signal.

The computed contour data can then directly be transmitted to a numerically controlled milling machine for making artificial teeth which are an exact fit. The artificial teeth may be permanently fixed or may be removable.

The advantage afforded by the process in accordance with the invention resides in that shapes of a tooth stump, the adjacent teeth and the antagonistic teeth can be optically detected and the resulting data can immediately be evalutated and used for a computation of the shape of the required artificial tooth. The process can be preformed quickly and in a simple manner in practice. The artificial tooth is made immediately without a need for an interval of time and for a making of contact impressions. As a result, the artificial tooth or teeth can be made and inserted during one visit.

In accordance with a desirable optional feature of the invention, at least three different patterns of horizontal or other contour lines are generated. In that case the artificial tooth or teeth can be made fully automatically.

The computation of the three-dimensional shapes of the tooth stump and of an artificial tooth is computed in accordance with the formula $$I = a \times (1 + m \times \cos \theta) \qquad (1)$$

wherein
I = intensity
a = background brightness
m = contrast
θ = angle

The intensity I can be measured and in a recording with a video camera will be determined for each picture element. In a video picture consisting, e.g., of 512×512 picture elements, information on the intensity of eahc picture element can be retrieved from the video signal. Three unknown variables remain in the equation and consist of the background brightness a, the constrast m and the angle θ, which the quantity that is to be found. When the angle θ has been determined for each picture element, the vertical coordinate (Z coordinate) can be calculated from that angle θ for each picture element because the vertical or Z coordinate is a function of θ. When the vertical or Z coordinate has been determined for each picture element by its X and Y coordinates, the three-dimensional shape of the tooth and of the artificial tooth has been determined. It will be understood that the vertical coordinate must be computed for each point that is defined by its X and Y coordinates. For that purpose it will be necessary and sufficient to compute the angle θ for each picture element defined by its X and Y coordinates. This will not be possible with the aid of equation (1) alone because it contains three unknown quantities, so that three equations will be required. In order to obtain said three equations, the pattern of horizontal or other contour lines must be displaced by a predetermined distance so that a pattern of horizontal or other contour lines will be generated which differs from the first pattern. That second pattern will be defined by the equation:

$$I_2 = a \times (1 + m \times \cos (\theta + O_2)) \qquad (2)$$

The angle $\theta_2$ resulting from the displacement is known because it is a function of the displacement of the lines. The unknown quantities a, m and θ are again contained in equation (2). The pattern of horizontal or other contour lines is then displaced once more. Whereas said vertical displacement preferably amount to one-fourth to one-third the line spacing of the grating, other well-defined displacements may be selected. The third pattern is defined by the equation:

$$I_3 = a \times (1 + m \times \cos (\theta + \theta_3)) \qquad (3)$$

The angle $\theta_3$ is known too because it is predetermined. The set of equations (1), (2) and (3) can now be used to compute the unknown quantity θ and the vertical coordinate Z for each picture element. When said method has been performed for each picture element, the entire three-dimensional shape has been computed.

With the aid of the method which has been described hereinbefore and which involves a "phase displacement" or a "displacement of lines", the artificial tooth or teeth can be made fully automatically. If only a single pattern of horizontal or other contour lines is detected and evaluated, it will be necessary to indicate by a manual entry the direction in which upper horizontal contour lines are spaced from lower ones and the direction in which lower horizontal contour lines are spaced from upper ones and also to indicate by a manual input the regions in which shadows or fissures are disposed. It will be understood that the process in accordance with the invention will give satisfactory results even when only a single pattern or horizontal or other contour lines has been generated but it will then be necessary to indicate by a manual entry the direction in which higher horizontal contour lines are spaced from lower ones and the regions in which shadows and fissures are contained. Such manual input may be effected by means of an interactive display terminal.

A manual entering of such additional information will not be required if three different patterns of horizontal or other contour lines are generated. In that case the Z coordinates for each picture element defined by its X and Y coordinates can be computed with the aid of the three equations (1), (2) and (3). No information will then be required on the direction in which higher horizontal contour lines are spaced from lower ones. The shadows and fissures can be detected in that case by the fact that they always appear at the same locations in the pictures of the three different patterns.

For a determination of the contour, at least three pictures are entered into the computer and the line pattern is displaced by a predetermined distance between the entry of each picture and the next. It will then be possible definitely to compute the contour from the amount of the displacement and the change of the intensity at each picture element.

DETAILED DESCRIPTION OF THE PREFERRED EMBODIMENTS

Illustrative embodiments of the invention will now be described in further detail with reference to the accompanying drawing.

Figure 1:
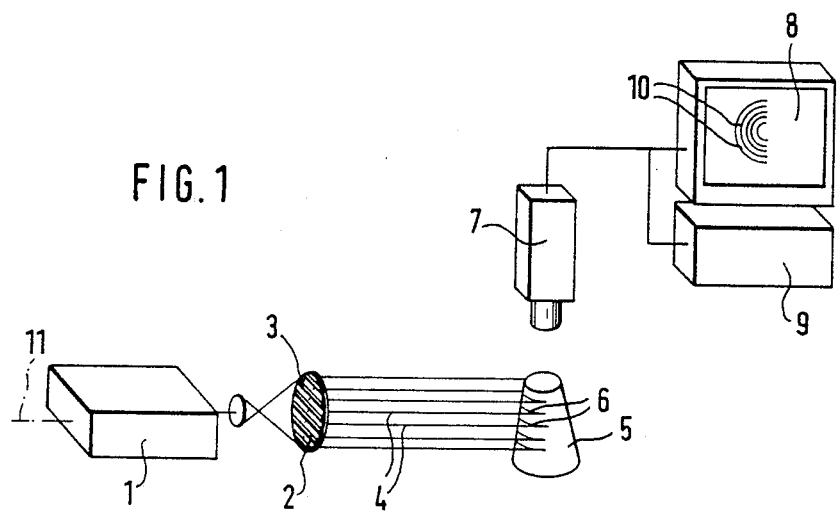
FIG. 1 illustrates the generation of contour lines by projection.

In accordance with FIG. 1, a projector 1 emits light rays, which are incident on a diffraction grating 2, which has horizontal opaque areas and horizontal light-transmitting areas 3, which have a predetermined and preferably equal spacing. As a result, light rays are emitted from the grating 2 in parallel horizontal planes 4 and are incident on the tooth stump 5, on which they generate horizontal contour lines 6. The horizontal contour lines 6 generated on the tooth stump 5 are recorded by a television camera 7, which delivers corresponding signals to a monitor and to a computer 9. The horizontal contour lines 6 can be displayed by the monitor 8, as is indicated at 10. From the intensity values for each of the picture elements of the monitor the computer 9 computes the three-dimensional shape of the tooth stump 5. The picture of the monitor may consist, e.g., of 512×512 picture elements.

If only a single picture of horizontal contour lines is to be recorded, it will be necessary to furnish the computer with the information indicating the direction in which the higher and lower portions of the tooth stump are spaced apart as well as with an indication of the areas in which shadows and/or fissures are disposed.

In a fully automatic system, a phase displacement or a displacement of lines is required. A picture of certain horizontal contour lines is recorded first. The projector 1 is then displaced by a well-defined vertical distance at right angles to the projection axis II, e.e., at right angles to the planes 4. That vertical distance preferably amounts to about one-fourth to one-thrid of the line spacing of the grating, i.e., of the spacing of the light-transmitting areas 3 of the grating 2. As a result, a second pattern of lines, which has been displaced from the first, is generated on the tooth stub 5 and is recorded by the television camera 7. That recording is repeated after a second displacement of the pattern of lines. As a result, information on three different patterns of horizontal contour lines is entered into the computer 9, which can fully automatically compute the three-dimensional shape of the tooth stump from that information. The shadows and/or fissures will be detected because they are disposed in the same areas in all three pictures whereas the horizontal contour lines are displaced. As a result, the computer 9 can automatically omit the data on said shadows and/or fissures in its computation.

When only a single picture of horizontal contour lines is recorded it will be necessary to furnish the computer 9 with additional information on the direction in which upper regions are spaced from lower ones and on the locations of any shadows and fissures. Such information can be entered by means of an interactive display terminal used as the monitor 8.

Figure 2:
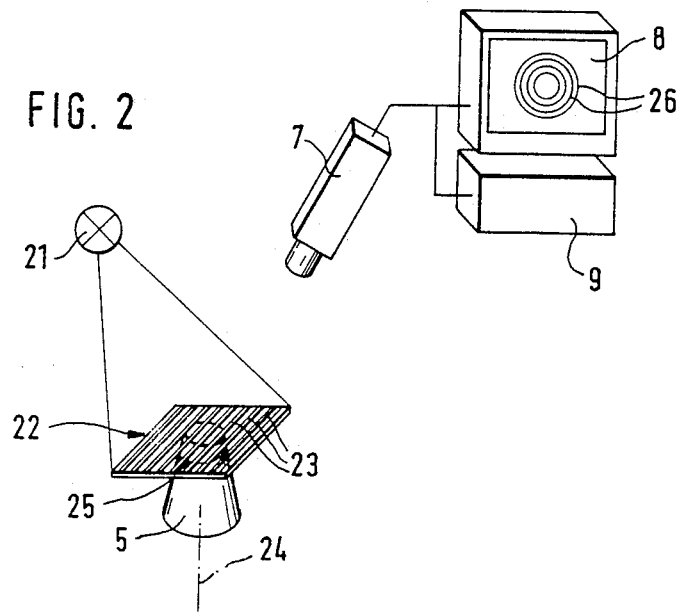
FIG. 2 illustrates the recording of contour lines with utilization of the moiré effect.

FIG. 2 shows the recording of contour lines with utilization of the moiré effect. A light source 21 emits light rays, which are incident on a diffraction grating 22, which consists of opaque areas and light-transmitting strips (lines) 23, which are parallel to each other and are spaced a well-defined, preferably uniform distance apart. The plane of the grating is at right angles to the axis 24 of the tooth stump 5. The light emitted by the grating generates contour lines on the tooth stump 5. Only one of said contour lines is shown in FIG. 2. The television camera 7 is located at a distance from the light source 21. In that arrangement the tooth stump 5 is illuminated through the grating 22 and is viewed by the television camera 7 through the same grating. The projected shadow pattern (contour lines 25) on the tooth stump 5 and the picture of the grating 22 are superimposed on each other in the camera 7 so that a moiré pattern is generated, which describes the contour of the tooth stump 5. That moiré pattern can be displayed by the monitor 8 as is indicated by lines 26. The television camera 7 is connected to the monitor 8 and to the computer 9.

The method illustrated in FIG. 2 differs from that of FIG. 1 only in that contour lines are generated by projection in the method of FIG. 1 and are recorded with utilization of the moiré effect in the method of FIG. 2. For this reason the description given in connection with the method of FIG. 1 is also applicable to the method illustrated in FIG. 2.

We claim:

1. A process of making artificial teeth comprising, generating horizontal or other contour lines on a ground tooth and on adjacent surfaces, acquiring data derived from said lines by optoelectronic means, computing the three-dimensional shapes of the tooth and of the required artificial tooth from said data in accordance with the formula $$I = a \times (1 + m \times \cos \theta) \tag{1}$$

wherein:
I = intensity
a = background brigthness
m = contrast
θ = angle,
and
forming an artificial tooth having the required shape as determined by said data.

2. A process according to claim 1, characterized in that the horizontal or other contour lines are generated by a projection process.

3. A process according to claim 1, characterized in that the horizontal or other contour lines are recorded with utilization of the moiré effect.

4. A process according to claim 1, characterized in that the horizontal or other contour lines are generated by shadow projection.

5. A process according to claim 1, characterized in that the horizontal or other contour lines are generated by interferometry by means of a laser.

6. A process according to claim 1, characterized in that the lines are recorded by means of a video camera.

7. A process of making artificial teeth comprising, generating horizontal or other contour lines on a ground tooth and on adjacent surfaces, acquiring data derived from said lines by optoelectronic means, computing the three-dimensional shapes of the tooth and of the required artificial tooth form said data, in accordance with the formula $$I = a \times (1 + m \times \cos \theta) \tag{1}$$

$$I_2 = a \times (1 + m \times \cos (\theta + \theta_2)), \text{ and} \tag{2}$$

$$I_3 = a \times (1 + m \times \cos (\theta + \theta_3)), \tag{3}$$

wherein
I, $I_2$, $I_3$ = intensity,
a = background brightness
m = contrast
θ, $\theta_2$, $\theta_3$ = angle,
and
forming an artificial tooth having the required shape as determined by said data.

8. A process according to claim 7, characterized in that the horizontal or other contour lines are generated by a projection process.

9. A process according to claim 7, characterized in that the horizontal or other contour lines are recorded with utilization of the moire effect.

10. A process according to claim 7, characterized in that the horizontal or other contour lines are generated be shadow projection.

11. A process according to claim 7, characterized in that the horizontal or other contour lines are generated by interferometry by means of a laser.

12. A process according to claim 7, characterized in that the lines are recorded by means of a video camera.

* * * * *